United States Patent [19]

Kaminsky et al.

[11] Patent Number: 4,971,940
[45] Date of Patent: Nov. 20, 1990

[54] TIN-CONTAINING COMPOSITION AND USE

[75] Inventors: Mark P. Kaminsky, Lisle; Mark S. Kleefisch, Plainfield; Gerry W. Zajac, Warrenville, all of Ill.

[73] Assignee: Amoco Corporation, Chicago, Ill.

[21] Appl. No.: 382,477

[22] Filed: Jul. 19, 1989

Related U.S. Application Data

[63] Continuation-in-part of Ser. No. 233,063, Aug. 17, 1988.

[51] Int. Cl.⁵ .................................................. C07C 5/48
[52] U.S. Cl. .................................... 502/300; 502/302; 502/340; 502/341; 502/349; 502/352
[58] Field of Search ............... 585/661, 663; 502/303, 502/306, 300, 340, 302, 341, 349, 352

[56] References Cited

U.S. PATENT DOCUMENTS

| | | | |
|---|---|---|---|
| 4,048,245 | 9/1977 | Pollitzer et al. | 260/668 |
| 4,444,984 | 4/1984 | Jones et al. | 585/500 |
| 4,560,821 | 12/1985 | Jones et al. | 585/500 |
| 4,608,449 | 8/1986 | Baerns et al. | 585/500 |
| 4,620,051 | 10/1986 | Kolts | 585/663 |
| 4,620,052 | 10/1986 | Kolts | 585/663 |
| 4,634,802 | 1/1987 | Jones et al. | 585/656 |
| 4,665,259 | 5/1987 | Brazdil et al. | 585/500 |
| 4,672,145 | 6/1987 | Kolts et al. | 585/658 |
| 4,705,772 | 11/1987 | Kolts | 502/303 |

*Primary Examiner*—Olik Chaudhuri
*Assistant Examiner*—James M. Hunter, Jr.
*Attorney, Agent, or Firm*—Nick C. Kottis; William H. Magidson; Ralph C. Medhurst

[57] ABSTRACT

A tin-containing composition is provided, the composition having a tin Auger line transition wherein the ratio of the area of the $M_5N_{4,5}N_{4,5}$ transition peak at 424.5 eV±1eV, having a 6 eV FWHM, to the area of $M_4N_{4,5}N_{4,5}$ transition peak at 430.5 eV±1eV is at least 10 to 1. Additional such tin-containing compositions, including catalyst compositions are also provided as are methods for converting feedstock alkanes containing from 1 to 4 carbon atoms to higher molecular weight hydrocarbons using such catalyst compositions.

28 Claims, 8 Drawing Sheets

COMPARISON OF Sn(MNN) AUGER SPECTRA

BINDING ENERGY (eV)

COMPARISON OF Sn(MNN) AUGER SPECTRA

COMPARISON OF Sn (MNN) AUGER SPECTRA

TIN-CONTAINING COMPOSITION AND USE

CROSS-REFERENCE TO RELATED APPLICATION

This application is a continuation-in-part of commonly assigned, copending U.S. patent application Ser. No. 233,063, filed August 17, 1988.

BACKGROUND OF THE INVENTION

This invention relates to novel tin-containing compositions and their use.

As the uncertain nature of ready supplies and access to crude oil has become increasingly apparent, alternative sources of hydrocarbons and fuel have been sought out and explored. The conversion of low molecular weight alkanes (lower alkanes) to higher molecular weight hydrocarbons has received increasing consideration as such low molecular weight alkanes are generally available from readily secured and reliable sources. Natural gas, partially as a result of its comparative abundance, has received a large measure of the attention focused on sources of low molecular weight alkanes. Large deposits of natural gas, and mainly composed of methane, are found in many locations throughout the world. In addition, low molecular weight alkanes are generally present in coal deposits and may be formed during numerous mining operations, in various petroleum processes, and in the above- or below-ground gasification or liquefaction of synthetic fuelstocks, such as coal, tar sands, oil shale and biomass, for example. In addition, in the search for petroleum, large amounts of natural gas are discovered in remote areas where there is no local market for its use as a fuel or otherwise. Additional major natural gas resources are prevalent in many remote portions of the world such as remote areas of western Canada, Australia, U.S.S.R. and Asia. Commonly, natural gas from these types of resources is referred to as "remote gas".

Generally much of the readily accessible natural gas is used in local markets as the natural gas has a high value use as a fuel whether in residential, commercial or industrial applications. Accessibility, however, is a major obstacle to the effective and extensive use of remote gas. In fact, vast quantities of natural gas are often flared, particularly in remote areas from where its transport in gaseous form is practically impossible.

Conversion of natural gas to liquid products is a promising solution to the problem of transporting low molecular weight hydrocarbons from remote areas and constitutes a special challenge to the petrochemical and energy industries. The dominant technology now employed for utilizing remote natural gas involves its conversion to synthesis gas, also commonly referred to as "syngas", a mixture of hydrogen and carbon monoxide, with the syngas subsequently being converted to liquid products. While syngas processing provides a means for converting natural gas to a more easily transportable liquid that in turn can be converted to useful products, the step of forming synthesis gas as an intermediate is typically relatively costly as it involves adding oxygen to the rather inert methane molecule to form a mixture of hydrogen and carbon monoxide. While oxygen addition to the carbon and hydrogen of methane molecules may be advantageous when the desired products are themselves oxygen containing, such as methanol or acetic acid, for example, such oxygen addition is generally undesirable when hydrocarbons such as gasoline or diesel fuel are the desired products as the added oxygen must subsequently be removed. Such addition and removal of oxygen naturally tends to increase the cost associated with such processing.

Methane, the predominant component of natural gas, although difficult to activate can be reacted with oxygen or oxygen-containing compounds such as water or carbon dioxide to produce synthesis gas. Synthesis gas can be converted to syncrude such as with Fischer-Tropsch technology and then upgraded to transportation fuels using usual refining methods. Alternatively, synthesis gas can be converted to liquid oxygenates which in turn can be converted to more conventional transportation fuels via catalysts such as certain zeolites.

Because synthesis gas processing requires high capital investment, with the syngas being produced in relatively energy intensive ways, such as by steam reforming where fuel is burned to supply heat for reforming, and represents an indirect route to the production of hydrocarbons, the search for alternate means of converting methane directly to higher hydrocarbons continues.

Oxidative coupling has been recognized as a promising approach to the problem of methane conversion although the mechanism of action is not, to date, completely understood. In such processes, methane is contacted with solid materials referred to by various terms including "catalyst", "promoters", "activators" or "contact materials", for example. Methane mixed with oxygen and catalyst is directly converted to ethane, ethylene, higher hydrocarbons and water. Carbon dioxide formation, which is highly favored thermodynamically, is an undesirable product associated with oxidative coupling as both oxygen and carbon are consumed without production of the desired higher value $C_{2+}$ hydrocarbons. In addition, many methods for oxidative conversion have been carried out in the absence of an oxygen-containing gas, theoretically relying on oxygen being supplied by the catalyst.

Catalytic mixtures of yttrium-barium-copper oxides are highly active and 100% selective for producing $CO_2$. Such catalysts which are highly selective for carbon dioxide formation are commonly referred to as "combustion catalysts". In order to obtain increased selectivity to hydrocarbon formation, Group IA metals, particularly lithium and sodium, have been added or otherwise used in many such catalytic mixtures. Under the conditions used for oxidative coupling, however, such mixtures typically realize migration and loss of the alkali metal. Thus, the need for highly active, $C_{2+}$ hydrocarbon selective and stable oxidative coupling catalyst and improved processes employing the same continues.

Many patents describe processes for converting methane to heavier hydrocarbons in the presence of reducible metal oxide catalysts. Most of these patents require or imply the need for a separate stage to re-oxidize the catalyst. These include U.S. Pat. No. 4,444,984 which teaches a reducible oxide of tin as a catalyst; U.S. Pat. No. 4,495,374 disclosing the use of any reducible oxide promoted by an alkaline earth metal; 4,523,049 showing a reducible oxide catalyst promoted by an alkali or alkaline earth metal, and requiring the presence of oxygen during the oxidative coupling reaction. U.S. Pat. No. 4,656,155 specifies yttrium in a mixture requiring zirconium and alkali metal. U.S. Pat. No. 4,450,310 claims coupling promoted by alkaline earth oxides in the total absence of molecular oxygen. U.S. Pat. No. 4,482,644 teaches a barium-containing oxygen-deficient catalyst with a perovskite structure. European patent application No. 198,251 covers a process conducted in the presence of free oxygen using a three component contact material of: (a) an oxide of calcium, strontium or barium, and optionally a material selected from the group consisting of chloride ions, compounds containing chloride ions, tin and compounds containing tin; (b) a sodium or potassium-containing material, and a Group IIA metal or a compound containing a Group IIA metal, and optionally a material selected from the group consisting of chloride ions, compounds containing chloride ions, tin and compounds containing tin; (c) a Group IA metal compound, and optionally a material selected from the group consisting of chloride ions, compounds containing chloride ions, tin and compounds containing tin.

U.S. Pat. No. 3,885,020, although disclosing contact materials of the oxidative coupling type, is directed to a method of converting hydrocarbons to $CO_2$ and water for pollution control. The combustion catalysts used consist of four components: (1) zirconium, tin or thorium; (2) an alkaline earth material; (3) a rare earth-type element such as scandium, lanthanum or cesium; and (4) a metal of the first transition series.

Baerns U.S. Pat. No. 4,608,449 relates to a methane conversion process using a suitable metal oxide catalyst, including tin oxide, on an oxide catalyst carrier carried out under temperatures of from 500° C. to 900° C. in the presence of oxygen at specified pressure.

Hicks U.S. Pat. No. 4,780,449 discloses a catalyst for the conversion of methane to hydrogen, and higher hydrocarbons comprising a non-reducible metal oxide of Be, Mg, Ca, Sr, Ba, Sc, Y, La, Pr, Nd, Sm, Eu, Gd, Tb, Dy, Ho, Er, Tm, Yb and Lu which may be used alone or with up to 50% by weight of one or more promoter oxides of Li, Na, K, Be, Mg, Ca, Sr, Ba, Sc, Y, La, Ce, Pr, Nd, Sm, Eu, Gd, Tb, Dy, Ho, Er, Tm, Yb, Lu, Sn, Pb, Sb, Bi, Cu, Ag and Au. Methane conversion is carried out at temperatures of from 500° to 1000° C.

Many analytical techniques have been developed to determine surface structure and/or composition of materials, e.g., solids. One such technique which has gained widespread application is Auger electron spectroscopy wherein electrons or photons, usually of 2 to 10 KeV, are used to excite core electrons of atoms of the solid with outer shell electrons "falling" into the electron vacancies created by the excited inner electrons. Such de-excitation of outer electrons into inner electron vacancies may lead to either an X-ray emission, or the energy may be given to another electron of the atom, commonly referred to as the Auger effect. Such Auger electrons have well-defined energies determined by the electron shells involved in the process, thus an Auger spectrum is characteristic of the atom and the environment about the atom. In Auger electron spectroscopy, the Auger electron is able to escape from the near surface region without appreciable energy loss; hence, the energy emission associated with such spectroscopy is primarily associated with surface or near surface atoms. Thus, one of the principal uses of Auger spectra is for the determination of the surface composition.

In general, quantum mechanics can be utilized to describe the discrete energy levels associated with the electrons of an atom. Thus, principal quantum numbers (n=1, 2, 3, 4 ...) correspond to electron shells (K, L, M, N ..., respectively). Auger notation builds on atomic electron shell notation, with subscripted numbers referring to the shell angular momentum state involved. Thus, subscript "1" refers to the s shell angular momentum state, subscripts "2" and "3" refer to the p1/2 or p3/2 shell angular momentum states, and subscripts "4" and "5" refer to the d3/2 or d5/2 shell angular momentum states, respectively, for example.

Auger transition notations are referred to by three capital letters; e.g., KLL, KLM, LMM, MNN, etc. The first letter in the notation refers to the electron shell in which the initial electron vacancy associated with the excitation of core electrons during Auger emission occurs, e.g., MNN indicates that the initial vacancy was in the M electron shell. The second letter in the notation refers to the shell from which an electron comes to fill the initial vacancy; e.g., MNN indicates an N electron "drops" to fill the "hole" in the M electron shell. The third letter refers to the shell from which the Auger electron (as described above) is emitted or ejected; e.g., MNN indicates that the Auger electron is expelled from the N shell.

Thus, the Auger transition notation $M_4N_{4,5}N_{4,5}$ means that the initial vacancy was in the M electron shell in the 3d3/2 state with the "hole" filled with a 4d electron from the N electron shell and a 4d electron from the N electron shell being expelled as the Auger electron. Conversely, the Auger transition notation $M_5N_{4,5}N_{4,5}$ is for an initial vacancy in the 3d5/2 state of the M electron shell with the same two types of 4d electrons involved in the Auger decay. Thus, the splitting of the two Auger features roughly would equal the spin orbit splitting of the 3d states.

SUMMARY OF THE INVENTION

It is an object of the present invention to overcome one or more of the problems described above.

According to the invention, an oxidized tin-containing composition is provided having a tin Auger line transition wherein the ratio of the $M_5N_{4,5}N_{4,5}$ transition peak at 424.5 eV±1 eV kinetic energy, having a 6 eV full width in eV at half maximum peak height (hereinafter referred to as "FWHM"), to the $M_4N_{4,5}N_{4,5}$ transition peak at 430.5 eV±1 eV kinetic energy is at least 10 to 1.

In one embodiment of the invention, such a tin-containing composition additionally including a Group IIA metal and oxygen is provided. The Group IIA metal preferably is magnesium, calcium, strontium or barium. In the composition, the tin and the Group IIA metal are present in an approximate atomic ratio of 2-4 atoms of tin per 0.5-3 atoms of Group IIA metal.

The invention also provides a process for converting a feedstock alkane containing from 1 to 4 carbon atoms to a higher molecular weight hydrocarbon. The process includes contacting a feedstock containing at least one alkane containing from 1 to 4 carbon atoms with a particular oxidative coupling catalyst in the presence of oxygen at oxidative coupling reaction conditions to produce a gaseous mixture including hydrocarbon products having higher molecular weight than the feedstock alkane from which they were formed. The particular oxidative coupling catalyst includes: (a) a Group IIA metal selected from the group consisting of magnesium, calcium, strontium and barium; (b) tin and (c) oxygen wherein the tin and Group IIA metal are in an approximate atomic ratio of 2-4 atoms of tin per 0.5-3 atoms of Group IIA metal with the catalyst having a tin Auger line transition wherein the ratio of the $M_5N_{4,5}N_{4,5}$ transition peak at 424.5 eV ±1 eV, having a 6 eV FWHM, to the $M_4N_{4,5}N_{4,5}$ transition peak at 430.5 eV ±1 eV is at least 10 to 1.

The invention also comprehends an oxidative coupling catalysts useful in such a process.

As used herein, references to Auger transition spectra peak ratios are to be understood as being based on the "area under" the respective peak or peaks. Herein, the areas under the various integrated Auger transition peaks are measured by a linear background subtraction method with, in the case of the Sn (MNN) Auger transition, the area of the 430.5±1 eV peak (the "first peak") being measured from the point of onset of the peak rise to the minimum point between the first peak and the 424.5±1 eV peak (the "second peak"), and the area of the second peak being measured in a similar fashion, from the minimum point between the first and second peaks to the end of the transition (roughly at 410 eV kinetic energy).

Further, references herein to energy peaks are to be understood to refer to kinetic energy (standardized to correct for charging electron emission and resulting surface charge build-up of the material) and not to binding energy.

Additionally, energy scales shown in the figures and referred to herein are those of binding energy relative to Al $K_\alpha$ radiation at 1486.3 eV.

Also, as used herein, the term "fresh catalyst" refers to a catalyst composition that has been calcined but has not subsequently been exposed to oxidative coupling reaction conditions, which conditions typically involve exposure at relatively high temperatures (as described later herein) to reactants such as low molecular weight alkanes, e.g., methane, and oxygen. Correspondingly, the term "used catalyst" refers to such of these compositions which have been exposed to such oxidative coupling reaction conditions. "Overreduced" oxidative coupling catalysts are those catalysts which have been irreversibly changed due to reducing conditions.

Other objects and advantages of the invention will be apparent to those skilled in the art from the following detailed description taken in conjunction with the appended claims and drawings.

Figure 11:
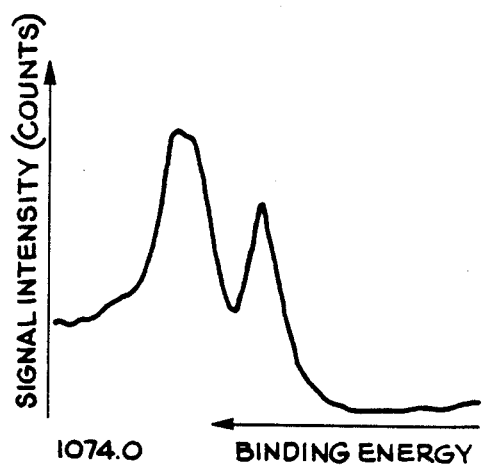
Figure 12:
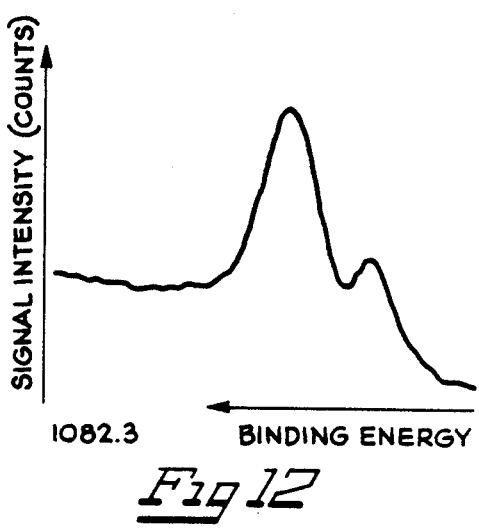
Figure 10:
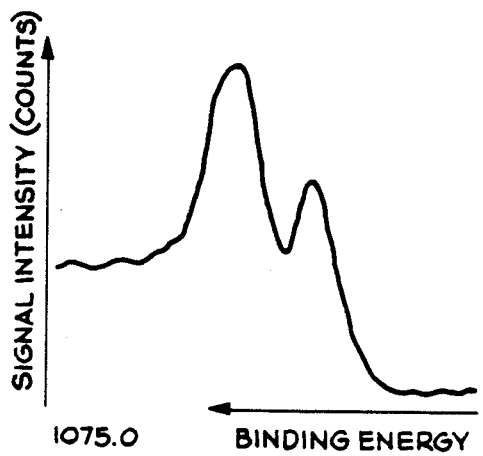
Figure 13:
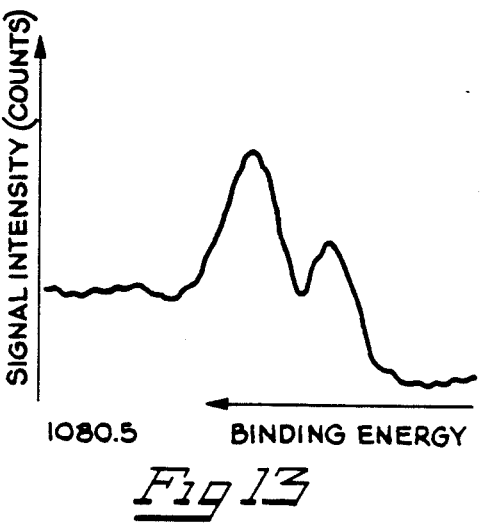

FIG is the Auger spectrum which shows the typical Sn MNN transition observed in SnO;

FIG. 11 is the Auger spectrum which shows the typical Sn MNN transition observed in $SnO_2$;

FIG. 12 is the Auger spectrum which shows the typical Sn MNN transition observed in $BaSnO_3$; and FIG. 13 is the Auger spectrum which shows the typical Sn MNN transition observed in $Y_2Sn_2O_7$.

DETAILED DESCRIPTION OF THE INVENTION

The present invention provides a novel, oxidized tin-containing composition as demonstrated by a novel tin Auger line transition. The oxidized tin-containing composition of the invention has a tin Auger line transition wherein the ratio of the $M_5N_{4,5}N_{4,5}$ transition peak at 424.5 eV ±1 eV, having a 6 eV FWHM, to the $M_4N_{4,5}N_{4,5}$ transition peak at 430.5 eV ±1 eV is at least 10 to 1 and generally in the range of 10 to 1 and to about 350 to 1 as will be described below.

In general, tin has found widespread use in many varying applications. More specifically, oxidized tin-containing compositions, such as forms of tin oxide, have been used in applications including as semiconductor electrodes or liquid crystal displays or use as a flame retardant, an abrasive, an additive to porcelain used in dental work, a glass additive to increase opacity and as a gas (e.g., carbon oxide, hydrogen and hydrocarbon) sensor. In addition, tin oxides are frequently utilized in many catalytic applications, such as the catalytic cracking of various large molecular weight petroleum feedstocks.

Figure 1:
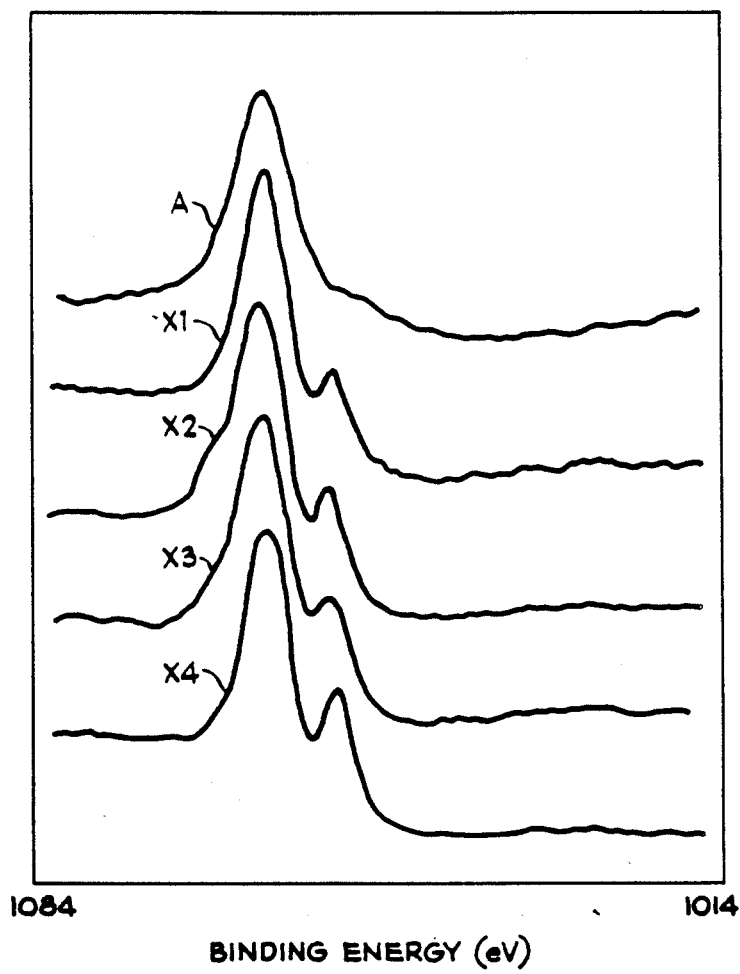
FIG. 1 is the Sn (MNN) Auger spectrum of a tin-containing composition of the invention (A) and those of other tin-containing compositions (X1-X4)

FIG. 1 presents the Sn (MNN) Auger spectrum of a tin-containing composition of the invention (A) as well as those of other tin-containing compositions (comparative compositions X1-X4). These compositions as well as the methods of their preparation are described below in Example 1.

As is evident in FIG. 1, the comparative tin-containing compositions X1-4 exhibit two peaks, one peak for the $M_5N_{4,5}N_{4,5}$ transition and the other for the $M_4N_{4,5}N_{4,5}$ transition, with the areas under each of these peaks being of about the same order of magnitude. The composition of the invention (Composition A), however, exhibits an Auger spectrum wherein the area under the $M_5N_{4,5}N4,5$ transition peak greatly exceeds the area under the $M_4N_{4,5}N_{4,5}$ transition peak.

Figure 2:
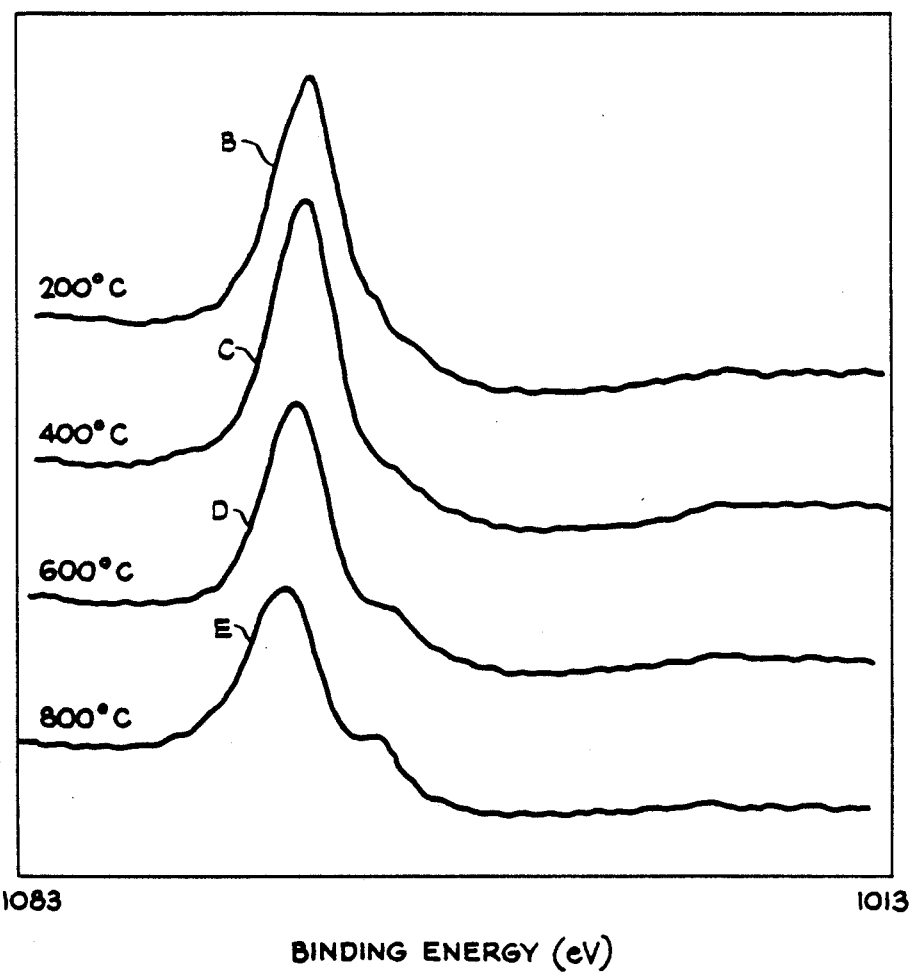
FIG. 2 is the Sn (MNN) Auger spectra of various oxidized tin-containing compositions of the invention, which compositions also contain oxidized barium.
Figure 3:
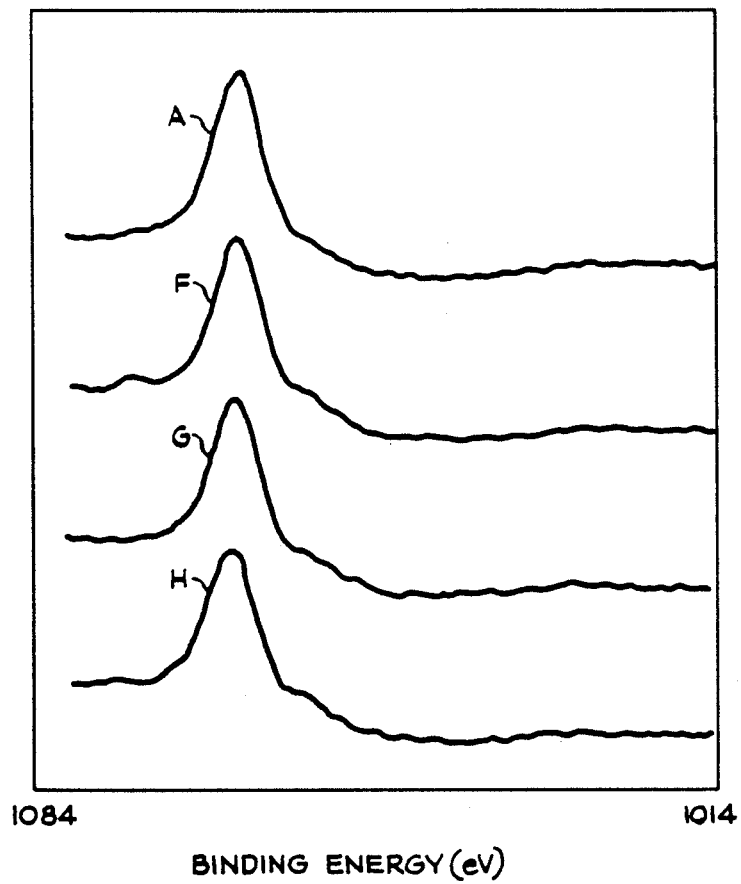
FIG. 3 is of Sn (MNN) Auger spectra of various oxidized tin-containing compositions of the invention, which compositions also contain oxidized yttrium and oxidized barium.

FIG. 2 presents the Sn (MNN) Auger spectra of various tin-containing compositions (B-E) of the invention, which compositions also contain barium and oxygen and for which compositions the method of preparation are described below (see Example 2). FIG. 3 represents the Sn (MNN) Auger spectra of composition A and various additional tin-containing compositions (F-H) of the invention, which compositions also contain the Group IIIB metal yttrium, the Group IIA metal barium and oxygen and for which compositions the method of preparation are described below (see Example 3). Each of the compositions has a peak at 424.5 eV ±1 eV, with this peak having about a 6 eV FWHM. Typically the Sn (MNN) Auger spectra of oxidized tin, whether alone or in tin-containing compositions such as described below and shown in FIGS. 8-13, exhibit a second peak at about 430.5 eV, with the ratio of the area of the first peak to the second peak ranging from about 4.8 to about 2.2.

While the oxidized tin-containing compositions of the invention may contain other elements or materials, the only material known to date to be required to be present is the oxidized tin itself. Other elements or materials which may be present in the compositions of invention include Group IIA metals such as magnesium, calcium, strontium and barium. Additionally, or in the alternative, Group IIIB metals such as yttrium, lanthanum and scandium, also preferably in an oxidized form, may be included.

In a preferred form the composition includes (a) a Group IIA metal of magnesium, calcium, strontium or barium (preferably barium), (b) tin and (c) oxygen. One such composition may be represented by the formula $BaSnO_y$ wherein y represents the number of oxygen anions required to balance the combined charge of the cationic species Ba and Sn.

In another preferred form, the composition includes: (a) Group IIIB metal selected from the group of yttrium, lanthanum, and scandium (preferably yttrium; (b) a Group IIA metal selected from the group of magnesium, calcium, strontium and barium (preferably barium); (c) tin and (d) oxygen wherein the tin, Group IIA metal and Group IIIB metal are present in an approximate atomic, ratio of 2–4 atoms of tin per 0.5–3 atoms of Group IIA metal per atom of Group IIIB metal.

In a preferred form of such a composition, wherein the Group IIIB metal is yttrium and the Group IIA metal is barium, the yttrium and barium and tin are present at an approximate atomic ratio of 1:2:3, respectively, and the composition is represented by the formula $Y_1Ba_2Sn_3O_y$ wherein y represents the number of oxygen anions required to balance the combined charge of cationic species Y, Ba and Sn when the cationic species barium is present solely as the oxide. When the cationic species is present as the carbonate, a preferred composition may be represented by the empirical formula $Y_1Ba_2Sn_3O_yC_z$ wherein z has a value of up to 2, and y represents the number of oxygen anions required to balance the combined charge of the cationic species, Y, Ba and Sn and three times the number of carbon atoms (i.e., 3z).

A preferred composition of the invention is represented by the formula $(Y_2O_3) (BaO)_{4-x} (BaCO_3)_x (SnO_2)_6$ wherein x is 0 when barium is present solely as an oxide and has a value of up to 4 when some of the barium species is present as the carbonate. For best results; it is preferred that the barium be present solely as an oxide, i.e., that x=0.

Forms of the oxidized tin-containing compositions of the invention which include an oxidized Group IIA metal selected from the group of magnesium, calcium, strontium and barium, with barium being particularly preferred, are useful in the conversion of feedstock alkanes containing from 1 to 4 carbon atoms to higher molecular weight hydrocarbons. Particularly preferred for use in the conversion of such feedstock alkanes which contain from 1 to 4 carbon atoms to higher molecular weight hydrocarbons are those compositions additionally comprising an oxidized Group IIIB metal selected from the group of yttrium, lanthanum and scandium. In particular, those of these compositions wherein the oxidized Group IIIB metal comprises yttrium and the oxidized Group IIA metal comprises barium have been found to be particularly useful for such conversions.

As described above, such processes are commonly referred to "oxidative coupling" processes. Certain compositions of the invention have been found useful as oxidative coupling catalysts and are relatively stable at oxidative coupling conditions, thereby offering an advantage over prior art technology.

In one aspect of the invention, a method for converting a feedstock alkane containing from 1 to 4 carbon atoms to form hydrocarbon products having higher molecular weights than the feedstock alkane from which they were formed comprising contacting a feedstock with a specified oxidative coupling catalyst in the presence of oxygen at oxidative coupling reaction conditions is provided. It is believed that process variable conditions including pressure, temperature, flow rate, feed gas composition and residence time can be widely varied within suitable parameters. Preferably, conditions should be chosen to cause oxygen conversion to proceed near to, but short of, completion in order to protect the catalyst from possible overreduction and degradation. This becomes particularly important at higher pressures and temperatures where increased catalytic activity may be compensated for by utilizing shorter contact times so as to avoid conditions at which complete oxygen conversion is realized. It is generally preferred to employ temperatures of from about 700° C. to about 900° C. and relatively low pressures, preferably pressures less than about 250 psig, and most preferably at about ambient pressure.

At temperatures up to about 800° C., residence times or relative feed rates are less critical. In operation, feed rates at room temperature and atmospheric pressure, e.g., feed rate/catalyst rate, may be varied from about 1000 cc/gm-hr to about 165,000 cc/gm-hr without substantially affecting catalyst performance.

The feedstock will generally include at least one alkane containing from 1 to 4 carbon atoms and, more preferably, comprises methane or natural gas with sulfur species removed and oxygen in premixed blends in ratios of about 2:1 to about 20:1 $CH_4$ to $O_2$. The feed may in addition include other species including nitrogen, carbon dioxide, carbon monoxide and water, for example.

The composition, referred to herein as a catalyst, may be maintained in the reaction zone as fixed, moving or fluidizing beds of solids. A fluidized bed operation is believed preferred because of its suitability in handling highly exothermic reactions like those involved in the oxidative coupling of methane.

The source of tin is believed to be extremely important. It is preferred to employ tin (II) acetate which contains a relatively large amount of excess acetic acid, e.g., the tin (II) acetate contains between about 5–15% acetic acid. One such tin acetate can be purchased from Alpha Products.

The tin-containing compositions of the invention which additionally include other components such as a Group IIA metal, oxygen and/or a Group IIIB, for example, can be prepared by process involving intimately mixing tin(II) acetate having a stoichiometric excess of acetic acid with an oxygen-containing compound of the Group IIA metal and/or an oxygen-containing compound of the Group IIIB metal, respectively.

In the case of the tin-containing compositions of the invention which also contain barium and oxygen or yttrium, barium and oxygen, such as may be use in oxidative coupling, a preferred method of preparation includes physically mixing tin (II) acetate with barium hydroxide or yttrium carbonate and barium hydroxide, respectively, and physically grinding the individual compounds together prior to calcining the mixture to a selected temperature. One skilled in the art and guided by the teachings herein may make appropriate calcining temperature selections without undue experimentation.

Another preferred method comprises preparing the yttrium, barium and tin-containing catalyst of the invention in the substantial absence of carbon oxides, such as under a nitrogen or purified air or other inert atmosphere. Best results may be achieved when both carbonates and $CO_2$ are prevented from contacting the catalyst during the early stages of preparation. A benefit of this procedure is believed to be catalysts with less variation in performance particularly when prepared in the absence of $CO_2$, such as which is normally present in air.

The following examples illustrate the practice of the invention. It is to be understood that all changes and modifications that come within the spirit of the invention are desired to be protected and thus the invention is not to be construed as limited by these examples.

EXAMPLES

Example 1

Method of composition preparation

Composition A

Tin (II) acetate, $Sn(C_2H_3O_2)_2$ (15.0g, 0.06335mole, from Alpha Products) was mixed with yttrium carbonate, $Y_2(CO_3)_3$-$3H_2O$ (4.12g, 0.01mole) and barium hydroxide, $Ba(OH)_2$-$8H_2O$ (12.74g, 0.0404mole) with a mortar and pestle. The solids were ground to a fine powder to homogenize these composition precursors. The hydroscopic nature of the solids resulted in the production of a white slurry upon grinding. After the slurry was thoroughly mixed, it was placed in a calcining furnace and heated to 700° C. at a rate of 4° C./min after which it was slowly heated to 800° C. at a rate of 2° C./min where in was held for five hours. The furnace was purged with a flow of air. The solid remained white after calcination. The preparation had a targeted composition of $YBa_2SN_3O_y$.

Comparative Composition X1

Barium oxide, BaO (46.47 g, 0.303 mole); yttrium oxide, $Y_2O_3$ (16.95 g, 0.0751 mole) and tin oxide, SnO (60.92 g, 0.452 mole) were mixed with a mortar and pestle. The powders were ground together for several minutes until they formed a homogeneous mixture. The mixture was then pelletized into a one inch diameter tablet and calcined in air using a clay crucible by placing the crucible in a calcining furnace and heated from 27° C. to 400° C. at a rate of 2° C./min, held at 400° C. for one hour, then heated to 800° C. at a rate of 2° C./min and held at 800° C. for five hours. It was then allowed to cool to room temperature.

The preparation had a targeted composition of $YBa_2Sn_3O_y$.

Comparative Composition X2

Barium hydroxide, $Ba(OH)_2$-$8H_2O$ (57.36 g, 0.1818 mole); yttrium carbonate, $Y_2(CO_3)_3$-$3H_2O$ (18.54 g, 0.045 mole) and tin oxalate, $SnC_2O_4$ (56.04 g, 0.271 mole) were mixed with a mortar and pestle. After mixing for several minutes the waters of hydration resulted in the formation of a damp, yellowish paste. The paste material was transferred to a clay crucible for calcination in air. The same calcination program as described above for Comparative Composition X1 was used.

The preparation had a targeted composition of $YBa_2Sn_3O_y$.

Comparative Composition X3

Barium hydroxide, $Ba(OH)_2$-$8H_2O$ (19.12g, 0.0606 mole); yttrium carbonate, $Y_2(CO_3)_3$ -$3H_2O$ (6.18 g, 0.015 mole) and tin ethyleleglycoxide, $SnO_2C_2H_4$ (16.16 g, 0.0904 mole) were mixed with a mortar and pestle. After mixing for several minutes a tan-colored homogenous mixture which maintained a powder consistency was formed. The powder mixture was transferred to a clay crucible and calcined in air.

The preparation had a targeted composition of $YBa_2Sn_3O_y$.

Comparative Composition X4

Barium oxide, BaO (46.47 g, 0.303 mole); yttrium oxide, $Y_2O_3$ (16.95 g, 0.0751 mole) and tin (IV) oxide, $SnO_2$ (67.90 g, 0.4506 mole) were mixed with a mortar and pestle. The powders were ground together to form a homogenous grey powder which was transferred to a clay crucible and calcined by heating from 27° C. to 700° C. at a rate of 4° C./min, held at 700° C. for one hour, then heated to 800° C. at a rate of 2° C./min and held at 800° C. for five hours. It was then allowed to cool to room temperature.

The preparation had a targeted composition of $YBa_2Sn_3O_y$.

Discussion

FIG. 1 presents the Sn(MNN) Auger spectra of Composition A and comparative compositions X1-4. As is evident from FIG. 1, although Composition A of the invention and the comparative tin-containing compositions X1-4 all had a targeted composition of $YBa_2Sn_3O_y$, the tin Auger line transition of the composition of the invention is readily discernible from those of the comparative examples as the comparative example compositions exhibit two peaks, with the areas under each of these peaks being of about the same order of magnitude whereas the composition of the invention (Composition A) exhibits an Auger spectrum wherein the area under the $M_5N_{4,5}N_{4,5}$ transition peak greatly exceeds the area under the $M_4N_{4,5}N_{4,5}$ transition peak.

Composition A of the invention has been found to be generally superior to comparative compositions such as X1-4 in terms of $C_2+$ hydrocarbon yield for the oxidative coupling of methane, when run under similar oxidative coupling conditions, e.g., a reaction temperature of about 750° C. to about 850° C. and a methane-to-oxygen feed ratio ranging between about 2:1 to about 10:1.

Example 2

Compositions B-E were each prepared following the same general procedure, a different calcining regime (as described below), however, was used for each of the compositions B-E.

Tin (II) acetate, $Sn(C_2H_3O_2)_2$ (10.17 g, 0.0423 mole) and barium hydroxide, $Ba(OH)_2$-$8H_2O$ (13.16 g, 0.0423 mole) were mixed with a mortar and pestle. The solids were ground to a fine powder to homogenize the precursors and after several minutes of mixing, the waters of hydration resulted in the formation of a creme-colored paste. This paste was then apportioned into four (4) alumina crucibles and was allowed to set and dry for a period of several hours, during which time the paste material hardened resulting in the creation of a dark metallic color at the material surface. Each of the crucibles were in turn subsequently placed in a calcining furnace and calcined using the described calcining regime:

B—Heated from 27° C. to 200° C. at a rate of 4° C./min. Held at 200° C. for 12 hours and then allowed to cool to room temperature.

C—Same as B but now heated to a temperature of 400° C.

D—Same as B but now heated to a temperature of 600° C.

E—Same as B but now heated to a temperature of 800° C.

Discussion

FIG. 2 presents the Sn (MNN) Auger spectra of compositions B-E. Each of these compositions has a peak at 424.5 eV ±1 eV, with this peak having about a 6 eV FWHM. Table I, below, reports the ratio of the area of the $M_5N_{4,5}N_{4,5}$ transition peak at 424.5 eV ±1 eV to the area of the $M_4N_{4,5}N_{4,5}$ transition peak at 430.5 eV ±1 eV, for the Sn(MNN) Auger spectra of these compositions.

TABLE I

| Compositions | $\left[\dfrac{\text{Area of } M_5N_{4,5}N_{4,5} \text{ transition peak}}{\text{Area of } M_4N_{4,5}N_{4,5} \text{ transition peak}}\right]$ |
| --- | --- |
| B | 333 |
| C | 111 |
| D | 33 |
| E | 15 |

For each of these compositions, the tin Auger line transition exhibits a ratio of the area of the $M_5N_{4,5}N_{4,5}$ transition peak at 424.5 eV ±1 eV to the area of the $M_4N_{4,5}N_{4,5}$ transition peak at 430.5 eV ±1 eV exceeding 10 to 1.

In fact, those of these compositions which were calcined at lower temperatures such as 600° C., 400° C. and 200° C., as in compositions D, C and B, respectively, exhibit peak area ratios substantially greater than 10 to 1, ranging up to about 350 to 1. Thus, for such compositions, the calcining temperature utilized in the preparation of the composition appears related to the area ratio of the $M_5N_{4,5}N_{4,5}$ transition peak to the $M_4N_{4,5}N_{4,5}$ transition peak for tin.

Example 3

Method of composition preparation

Composition A

The preparation of composition A is described above in Example 1.

Composition F

Same as that of composition A.

Compositions G and H

Same as A but now heated to a calcining temperature of 900° C. and 1000° C., respectively.

Discussion

FIG. 3 represents the Sn (MNN) Auger spectra of compositions A and F-H. Table II, below, reports the ratio of the area of the $M_5N_{4,5}N_{4,5}$ transition peak at 424.5 eV ±1 eV to the area of the $M_4N_{4,5}N_{4,5}$ transition peak at 430.5 eV ±1 eV, for the Sn(MNN) Auger spectra of these compositions.

TABLE II

| Compositions | $\left[\dfrac{\text{Area of } M_5N_{4,5}N_{4,5} \text{ transition peak}}{\text{Area of } M_4N_{4,5}N_{4,5} \text{ transition peak}}\right]$ |
| --- | --- |
| A | 132 |
| F | 71 |
| G | 49 |
| H | 37 |

As with compositions B-E in Example 2, the compositions A and F-H each exhibit a tin Auger line transition wherein the ratio of the specified peak areas exceed 10. This is in contrast to the spectra of compositions X1-4 of Example 1 and FIG. 1 wherein this ratio is below 10 and the Sn (MNN) Auger spectra of oxidized tin shown in FIGS. 8-13 wherein this ratio generally ranges from about 4.8 to about 2.2.

Example 4

Composition A of Example 1 was placed in a 9 mm internal diameter quartz tube reactor having a 3 mm outside diameter quartz thermowell. A premixed gas blend containing 40% by volume of methane, 4% by volume of oxygen and an inert carrier was employed. Nitrogen was used as an internal standard for conducting mass balances. 40–60 Mesh quartz (Vycor) was used to dilute the 14–40 mesh catalyst loading to obtain a more nearly isothermal bed. A relative feed rate of 1000 cc standard (at room temperature and pressure) of feed per hour per gram of catalyst was employed. Product gases were recycled to the front of the reactor and combined with fresh feed at a ratio of about 10:1 recycle to fresh feed. Methane conversion was determined by differences in outlet and inlet molar rates and also by moles of products formed. Oxygen was nearly completely consumed (98%+) for temperatures of from 600° to 750° C. $C_2+$ selectivity improved with increasing temperatures and reached about 50% at 750° C. The only other major carbon-containing product was $CO_2$.

Example 5

Composition A of Example 1 was retested following the method of Example 4 at a fixed temperature of 750° C. and relative feed rates (feed rate/catalyst weight) of about 5, 10 and 15 times that used in Example 4. Even at these increased feed rates, oxygen consumption remained high (92–98%). $C_2+$ selectivity was relatively insensitive to these variations.

Example 6

Composition A of Example 1 was tested at higher feed rates and temperatures, without recycling product gases. The feed composition was also varied. The reaction conditions are summarized below in Table III.

TABLE III

| Run | $CH_4:O_2$ | Space Velocity (cc/gm-hr) | Max Temp, °C. |
| --- | --- | --- | --- |
| 1 | 2:1 | 24,000 | 750 |
| 2 | 10:1 | 42,000 | 850 |

TABLE III-continued

| Run | CH$_4$:O$_2$ | Space Velocity (cc/gm-hr) | Max Temp, °C. |
|---|---|---|---|
| 3 | 10:1 | 48,000 | 875 |

The first run showed little catalyst performance change over a 20 hour testing cycle. The feed was changed to a higher CH$_4$:O$_2$ ratio for runs 2 and 3. At 850° C. in run 2, selectivity to C$_2$+ reached about 68% with CO$_2$ making up most of the balance. Even at the high relative feed rates, near full oxygen conversion was observed. In run 3, both temperature and feed rate were increased. The catalyst began to change significantly at 875. When the temperature was lowered to 850° C. after having been at 875° C., the catalyst showed a significant loss in C$_2$+ selectivity.

Example 7

Bulk metals analysis of fresh and used Y$_1$Ba$_2$Sn$_3$O$_y$ catalyst prepared by the method of Composition A of Example 1 was conducted using x-ray fluorescence (XRF). The results are listed below in Table IV. As can be seen, for samples 1 and 2, the Ba and Sn ratio and the elemental compositions for all three elements are within 10% of the fresh catalyst composition. For example 3, a correction must be applied due to the probable effect of the catalyst bed diluent used in the reactor test. Using the yttrium elemental analysis to estimate diluent amount, one must multiply the analyses by about 1.5 to get corrected value. After doing so, the Sn value is within 10% of the fresh catalysts and the Ba value within 15% of the fresh catalyst value. Thus, large, i.e. greater than 20%, losses of the elements are not observed with use.

TABLE IV

| Sample | % Y | % Ba | % Sn | Stoichiometry |
|---|---|---|---|---|
| 1 (used) | 9.5 | 31 | 34 | Y$_1$Ba$_{2.1}$Sn$_{2.68}$ |
| 2 (used) | 9.9 | 33 | 39 | Y$_1$Ba$_{2.16}$Sn$_{2.95}$ |
| 3 (used) | 6.4 | 18.2 | 22.5 | Y$_1$Ba$_{1.84}$Sn$_{2.63}$ |
| 4 (fresh) | 9.6 | 32 | 37 | Y$_1$Ba$_{2.16}$Sn$_{2.89}$ |

As expected, the tin is lower than targeted due to the presence of excess acetate in the tin acetate starting material. Not much difference was observed between some of the used catalyst and fresh catalyst indicating no large-scale metal leaching or volatilization.

Example 8

Y$_1$Ba$_2$Sn$_3$O$_y$ catalyst (50 mg), prepared by the method of Composition A of Example 1, was crushed to 80-100 mesh and diluted 15:1 with alumina and evaluated to determine oxygen conversion as a function of catalytic contact time (weight of catalyst per flow rate of gas feed) and temperature. Tests were conducted at 5 psig outlet and feed composition of 40% methane+4% oxygen+56% nitrogen. The tests were conducted in the order of lowest to highest temperature. Standard conditions (750° C., 5 psig, 25 sccm =0.120 g catalyst-sec/cc feed at STP) were repeated after each temperature to assure that catalyst performance remained unchanged. The results are set forth in Table V below.

TABLE V

Repeat of Standard Conditions (750° C., 5 psig, 0.12 g cat-sec/cc, 56% N$_2$ + 40% CH$_4$ + 4% O$_2$)

| Condition | % Oxygen Conversion | % C$_2$+ Selectivity |
|---|---|---|
| Start-of-Run 750° C. | 88 | 55 |
| After Running at 775° C. | 88 | 54 |
| After Running at 800° C. | 86 | 53 |
| After Running at 825° C. | 89 | 54 |
| After Running at 875° C. | 87 | 52 |

At 750° C., C$_2$+ selectivity was relatively insensitive to oxygen conversion until reaching complete conversion, upon which C$_2$+ selectivity began to drop dramatically.

At 800° C., C$_2$+ selectivity declines as contact time increases, even at oxygen conversions of less than 100%. At the end of the run with 0.05 g of catalyst, C$_2$+ selectivity had declined about 65% at a contact time of 0.012 g catalyst-sec/cc gas.

At 850° C., C$_2$+ selectivity drops dramatically as contact time is increased.

Example 9

Three samples of Y$_1$Ba$_2$Sn$_3$O$_y$ catalyst, A', A" and A''', respectively, were prepared by the method of Composition A of Example 1 except the calcination temperatures of A" and A''' were 1100° C. and 1550° C., respectively. Catalyst A' was calcined at 800° C. as in Example 1. Testing of these three catalysts under the same conditions of 250 mg catalyst, 100 standard cc per minute of a preblended gas containing about 15% CH$_4$, 7.5% O$_2$, and balance N$_2$, at 750° C. gave the performance shown in Table VI.

TABLE VI

| Catalyst | Conversion % O$_2$ | Conversion % CH$_4$ | % C$_2$+ Selectivity |
|---|---|---|---|
| A' | 95 | 27 | 22 |
| A" | 100 | 29 | 20 |
| A''' | 20 | 5 | 0 |

For best performance in oxidative coupling, the catalysts should be calcined below 1550° C. and preferably at less than 1100° C.

Example 10

The effects of varying methane-to-oxygen ratio on performance of the catalyst of Composition A of Example 1 was investigated in a plug-flow reactor using 50 mg of catalyst at 5 psig, 100 sccm CH$_4$, 0 or 135 sccm N$_2$ which corresponds to 0% or 56% at nitrogen dilution, respectively, at both 750° C. and 800° C. The results are summarized in Tables VII and VIII below.

TABLE VII

Effect of Varying Methane-to-Oxygen Ratio on Performance with Y$_1$Ba$_2$Sn$_3$O$_y$ at 750° C.

| | | Methane-to-Oxygen Ratio | | |
|---|---|---|---|---|
| | | 5:1 | 10:1 | 18:1 |
| % Conversion | | | | |
| O$_2$ | 56% N$_2$ Dilution | 33 | 42 | 57 |
| | w/o N$_2$ | 49 | 62 | 77 |
| | 56% N$_2$ Dilution | 5.2 | 4.5 | 4.2 |

TABLE VII-continued

Effect of Varying Methane-to-Oxygen Ratio on Performance with $Y_1Ba_2Sn_3O_y$ at 750° C.

| | | Methane-to-Oxygen Ratio | | |
|---|---|---|---|---|
| | | 5:1 | 10:1 | 18:1 |
| $CH_4$ | w/o $N_2$ | 8.7 | 6.7 | 5.2 |
| % Selectivity | | | | |
| $C_2+$ | 56% $N_2$ Dilution | 42 | 54 | 62 |
| | w/o $N_2$ | 38 | 52 | 64 |
| $C_3+$ | 56% $N_2$ Dilution | 0.9 | 1.3 | 1.6 |
| | w/o $N_2$ | 1.2 | 1.9 | 2.3 |
| $C_2H_4$ to $C_2H_6$ ratio | 56% $N_2$ Dilution | 0.19 | 0.17 | 0.16 |
| | w/o $N_2$ | 0.41 | 0.34 | 0.29 |

TABLE VIII

Effect of Varying Methane-to-Oxygen Ratio on Performance with Y—Ba—Sn—O Catalyst at 800° C.

| | | Methane-to-Oxygen Ratio | | |
|---|---|---|---|---|
| | | 5:1 | 10:1 | 18:1 |
| % Conversion | | | | |
| $O_2$ | 56% $N_2$ Dilution | 59 | 74 | 89 |
| | w/o $N_2$ | 83 | 93 | 99 |
| $CH_4$ | 56% $N_2$ Dilution | 12.7 | 10.2 | 7.6 |
| | w/o $N_2$ | 16.4 | 11.7 | 7.8 |
| % Selectivity | | | | |
| $C_2+$ | 56% $N_2$ Dilution | 57 | 68 | 74 |
| | w/o $N_2$ | 53 | 67 | 76 |
| $C_3+$ | 56% $N_2$ Dilution | 3.0 | 3.4 | 3.1 |
| | w/o $N_2$ | 3.5 | 4.6 | 4.3 |
| $C_2H_4$ to $C_2H_6$ ratio | 56% $N_2$ Dilution | 0.49 | 0.40 | 0.31 |
| | w/o $N_2$ | 0.94 | 0.68 | 0.50 |

The data show that methane-to-oxygen ratios and temperature have significant impacts on conversion and selectivity. On the other hand, nitrogen dilution has little effect on $C_2+$ selectivity and appears to play a secondary role on conversion, presumably a kinetic rate effect, from altering reactant partial pressures. As the methane-to-oxygen ratio increases, methane conversion decreases whereas $C_2+$ selectivity increases. The yield of $C_2+$ hydrocarbons is simply the product of selectivity and conversion. The $C_3+$ selectivity was slightly higher without nitrogen dilution.

EXAMPLE 11

$Y_1Ba_2Sn_3O_y$ catalyst prepared by the method of composition A of Example 1 was analyzed by XPS to determine metal ratios and oxidation states. Surface compositions, atomic ratios and electron binding energies (ebe's) are reported in Tables IX–XI.

TABLE IX

Relative Atomic Percent of $Y_1Ba_2Sn_3O_y$ Catalyst

| Run | O | $C_{total}$ | $C_{CO_3}$ | Y | Ba | Sn |
|---|---|---|---|---|---|---|
| 1 | 50.8 | 10.7 | 1.6 | 14.7 | 8.8 | 14.9 |
| 2 | 47.5 | 25.1 | 3.8 | 8.0 | 6.4 | 13.0 |
| 3 | 55.6 | 6.1 | 1.2 | 10.8 | 9.9 | 17.6 |

TABLE X

XPS Surface Stoichiometry

| | Target | | | Experimental | | |
|---|---|---|---|---|---|---|
| Run | Y | Ba | Sn | Y | Ba | Sn |
| 1 | 1 | 2 | 3 | 1 | 0.60 | 1.00 |
| 2 | 1 | 2 | 3 | 1 | 0.79 | 1.62 |
| 3 | 1 | 2 | 3 | 1 | 0.93 | 1.64 |

TABLE XI

Electron Binding Energies (eV) of $Y_1Ba_2Sn_3O_y$ Catalyst

| Run | O 1s | % | C 1s | % | Y 3d5/2 | % |
|---|---|---|---|---|---|---|
| 1 | 528.1 | 65 | 284.6 | 85 | 156.4 | 100 |
| | 530.5 | 35 | 288.8 | 15 | | |
| 2 | 528.8 | 50 | 284.6 | | 156.2 | 100 |
| | 531.0 | 50 | 288.3 | | | |
| 3 | 529.3 | 60 | 284.7 | 61 | 156.4 | 100 |
| | 531.3 | 40 | 285.9 | 17 | | |
| | | | 289.5 | 22 | | |

| Run | Ba 3d5/2 | % | Sn 3d5/2 | % |
|---|---|---|---|---|
| 1 | 778.0 | 100 | 483.7 | 20 |
| | | | 485.6 | 80 |
| 2 | 778.2 | 100 | 485.4 | 100 |
| 3 | 778.6 | 100 | 485.9 | 100 |

Repeat analyses on three portions of the sample gave variable compositions (Table IX) indicating heterogeneity of the fresh catalyst. Yttrium surface enrichment, as indicated by the Sn/Y and Ba/Y ratios of Table X, causes the Y:Ba:Sn ratios to differ from the target bulk value 1:2:3. The ratios obtained from the three samples vary slightly; yet, they reflect barium and tin depletion. Note, for instance, that the first run in Table X has a stoichiometry consistent with the tin pyrochlore ($Y_2Sn_2O_7$) which has been identified by X-ray diffraction (XRD). Tin is present in two or three chemical states, Sn 3d 5/2 ebe's of 483.7 eV and 485.6 eV indicates elemental tin (20%) and $Sn^{+2}$ and/or $Sn^{+4}$ (80%) respectively (Table XI). This result is in excellent agreement with XRD data. Only one portion of the three analyzed contained elemental tin. This could be indicative of tin oxidation or sample heterogeneity. The Sn 3d ebe's are usually low when compared to literature and experimental XPS data of the pure compounds, indicating that tin formed a compound with yttrium and barium. The Ba 3d 5/2 of 778.2 eV is too low to indicate the presence of $BaCO_3$ and BaO (ebe's 779.0 and 779.7 eV, respectively) as reported in Table XI. Y 3d ebe's of all samples were at 156.5 ±0.3 eV. Literature reports the same values for $Y_2O_3$. Two oxygen species with ebe's at approximately 528.1 and 530.0 eV were found. The former species is typical for metal oxides. The latter is too low for adsorbed oxygen and could be representative for the specific compound formed by barium, tin and yttrium.

Example 12

A portion of a sample of the catalyst of Composition A of Example 1 was mounted on a scanning electron microscope (SEM) stub. In addition, another portion of sample was embedded in epoxy and the cross-section exposed by grinding and polishing and also by cutting the embedded sample with a diamond knife on the ultramicrotome. The sample was then examined in the SEM uncoated, and subsequently coated with gold in the vacuum evacuator. At ×10,000 magnification, the areas examined of the uncoated sample show grainy particles ranging in size from 500 Å to 3000 Å in diameter. Some of the crystals appeared to be oriented perpendicular to the plane of the other crystals.

SEM-EDX elemental analysis dot maps were obtained of the cross-section areas. Y and Ba appear uniformly distributed, but the Sn rich areas appear to be concentrated in small clumps throughout the sample.

Example 13

A long term stability test was conducted in a recycle reactor wherein the reactor gases were well backmixed with 50 mg of the $Y_1Ba_2Sn_3O_y$ catalyst of Composition A of Example 1 at 750° C., 3 psig and 120,000 cc/gm-hr SV of 40% $CH_4$+4% $O_2$ +56% $N_2$. The run lasted nearly 10 days without any change in selectivity or conversion, other than that accountable by changing feed gas cylinders. Studies of the used catalyst are described below.

Studies have shown that there are several characteristics of such $Y_1Ba_2Sn_3O_y$ metal oxide catalysts that classify it as a unique composition. STEM/EDX characterization showed a distinct change in the homogeneity of the composition throughout the used catalyst compared to fresh catalysts. Depending on the reaction conditions, varying degrees of homogeneity could be obtained with the most homogeneous samples being produced under total oxygen conversion or above 875° C. When coupled with XRD analysis, the STEM/EDX data present a model of the catalyst being a crystalline barium stannate ($BaSnO_3$) which is coated or in solid solution with an amorphous oxide/carbonate mixture of yttrium and barium, represented by $YBaC_zO_y$. The resulting mixture is unique.

To illustrate this increase in homogeneity of the used catalyst, the composition at several points in the catalyst, as determined by STEM/EDX, was plotted on a ternary phase diagram. In FIGS. 4-7, $YO_{1.5}$, BaO, and $SnO_2$ are at the three corners and the composition at any point in the diagram can be determined where the point intersects the tie lines for each of the elements. The tie lines are in the units of mole %. For example, a composition represented by the point in the phase diagram that intersects the 30% line of BaO, the 20% line of $YO_{1.5}$ and the 50% line of $SnO_2$ has 30 mole % BaO, 20 mole % $YO_{1.5}$ and 50% $SnO_2$, or $Y_1Ba_{1.5}Sn_{2.5}$.

Figure 4:
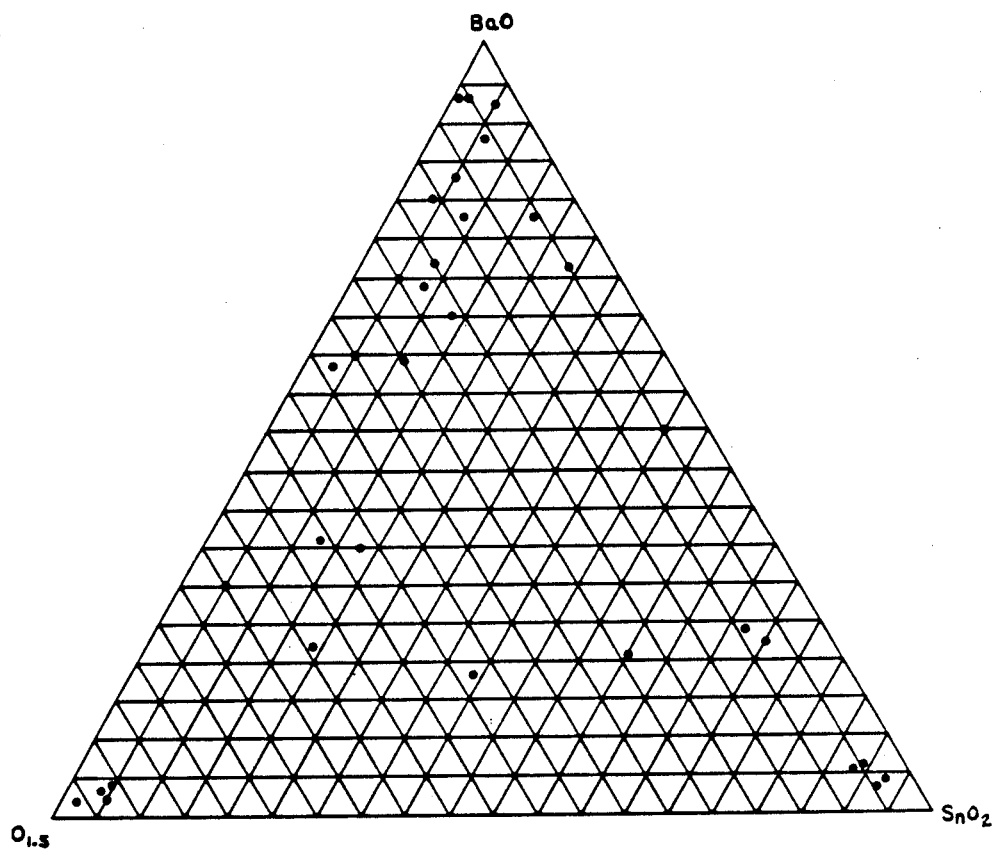
FIG. 4 is a ternary phase diagram, as derived by STEM/EDX, of fresh $Y_1Ba_2Sn_3O_y$ catalyst composition.

Referring to the drawings, FIG. 4 is a STEM/EDX ternary phase diagram of the distribution of compositions observed in the fresh $Y_1Ba_2Sn_3O_y$ catalyst. A large degree of scatter indicates the heterogeneity of the catalyst. Virtually pure BaO, $Y_2O_3$ and $SnO_2$ were observed along with mixtures of the three metal oxides.

Figure 5:
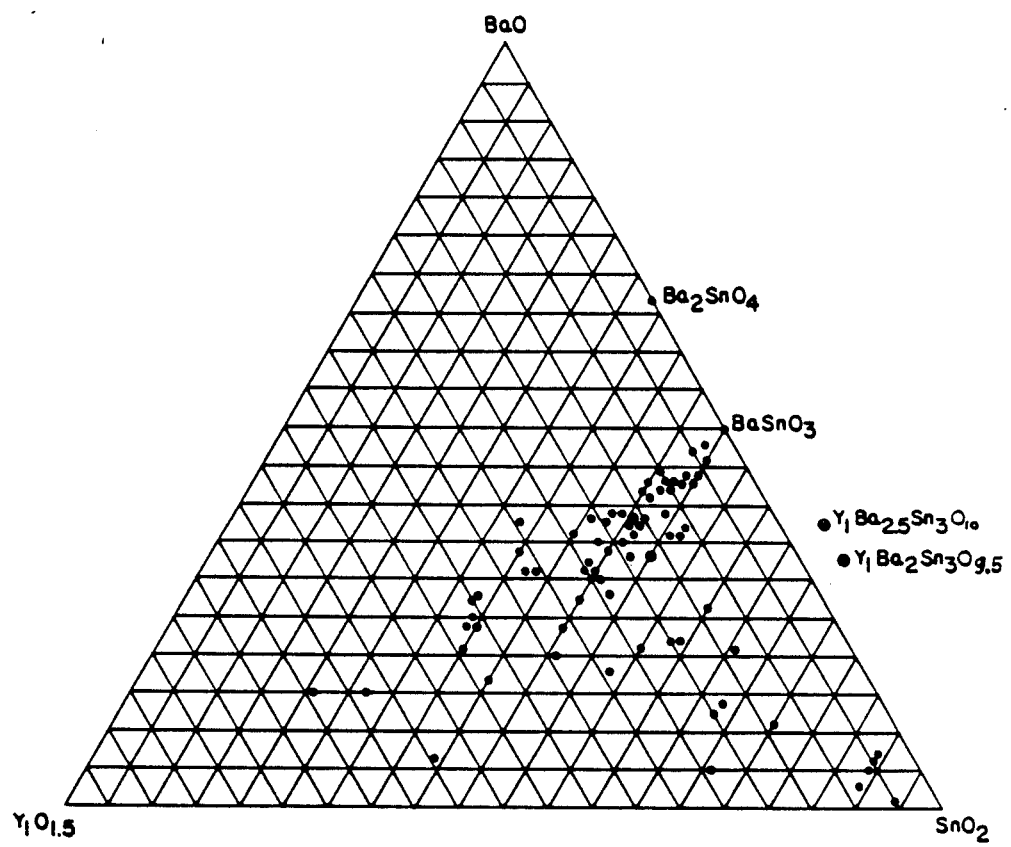
FIG. 5 is a ternary phase diagram, as derived by STEM/EDX, of used $Y_1Ba_2Sn_3O_y$ catalyst that has not been exposed to reducing conditions.

FIG. 5 is a STEM/EDX ternary phase diagram of a used catalyst that has not been exposed to reducing conditions.

A majority of the compositions falls on the tie line between $BaSnO_3$ and $YO_{1.5}$ and the region below it. Many areas converge around the $Y_1Ba_2Sn_3O_y$ nominal composition even though there is no crystalline phase with this composition. $BaSnO_3$ is the major phase in this material with minor amounts of $SnO_2$ which are also observed by STEM/EDX. The only way areas can have a composition of $Y_1Ba_2SnO_3$ is to have an amorphous coating or solid solution of yttria, barium, carbonates and tin oxides on crystalline $BaSnO_3$.

Figure 6:
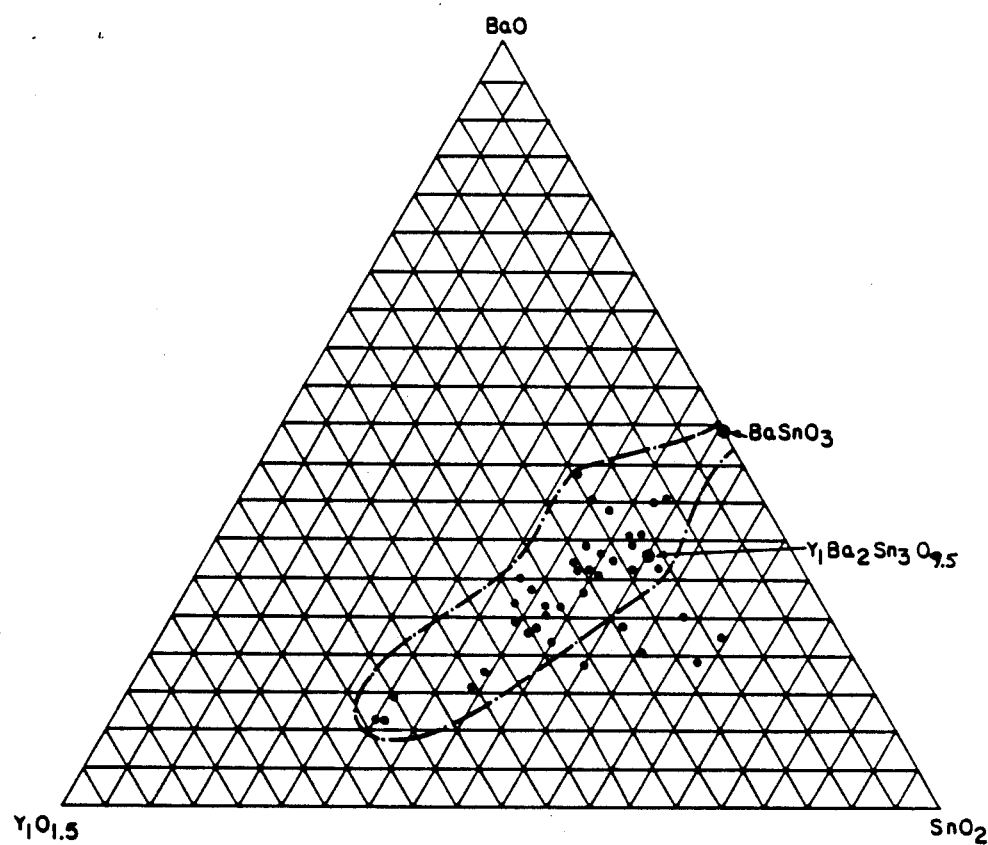
FIG. 6 is a ternary phase diagram, as derived by STEM/EDX, of used $Y_1Ba_2Sn_3O_y$ catalyst that has been exposed to reducing conditions.

FIG. 6 is a ternary phase diagram of a catalyst that has been exposed to reducing conditions (100% $O_2$ conversion) at 750° C. The homogeneity of the composition has increased in this sample such that most areas fall just below the $BaSnO_3$, $YO_{1.5}$ tie line and in closer proximity to the crystalline phase so the majority of the areas contain a crystalline $BaSnO_3$ which is coated or in solid solution with an amorphous oxide/carbonate mixture of yttrium and barium.

Figure 7:
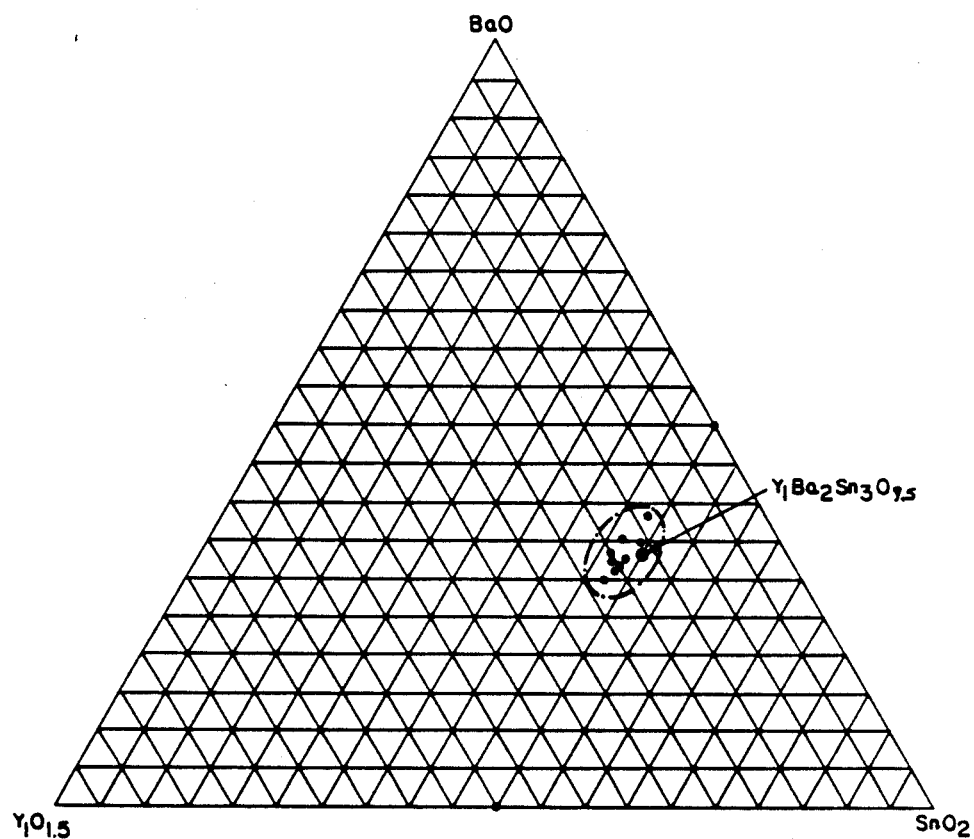
FIG. 7 is a ternary phase diagram, as derived by STEM/EDX, of used $Y_1Ba_2Sn_3O_y$ catalyst that has been exposed to severe reducing conditions.

FIG. 7 is a STEM/EDX ternary phase diagram of a catalyst that has been exposed to severe reducing conditions. Extreme reducing conditions at 875° C. further homogenized the catalyst composition as seen in FIG. 4. The distribution centers exclusively on the $Y_1Ba_2Sn_3O_y$ composition even though by XRD, the major crystalline phase is $BaSnO_3$.

The region of the phase diagram that the composition of the used catalyst falls in is:

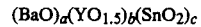

$$(BaO)_a(YO_{1.5})_b(SnO_2)_c$$

wherein 5%<a<50%; 0%<b <57%; and 25%<c<90%.

Depending upon the catalyst preparation, XPS analysis of the catalyst indicates apparent enrichment of the surface with either barium in the form of carbonate or oxide or yttria. Smaller amounts of tin were detected on the surface in part due to the Sn aggregating into small $SnO_2$ particles. Auger line shape analysis of the Sn MNN transition of the fresh catalyst indicates the Sn is in a unique environment. Unusually high hydrogen consumption was observed in the TPR/TPO analysis of $Y_1Ba_2Sn_3O_y$ catalyst along with trends in reduction temperature versus catalyst activity. All of these unique characteristics are described more fully in the following examples.

Example 14

Analytical electron microscopy shows distinct differences in fresh and used $Y_1Ba_2Sn_3O_y$ catalysts which evidence the unique nature of the material. A histogram of selected areas were analyzed in both the fresh and used catalysts by Energy Dispersive X-Ray (EDX) in the STEM mode. After calibrating with known standards, the metal composition could be quantitated in these different areas. A fresh catalyst was very heterogeneous in composition with regions of pure $BaCO_3$, $SnO_2$ and $Y_2O_3$ observed along with mixtures of the various elements. Depending on the reaction conditions, the catalyst becomes more homogeneous in Y, Ba and Sn composition. Severe reaction conditions such as total oxygen conversion and greater than 875° C. reaction temperatures cause the most dramatic changes and also caused the catalyst to lose selectivity to $C_2+$. Virtually all particles analyzed had close to the nominal composition $Y_1Ba_2Sn_3O_y$. This is unusual in that the XRD showed only $BaSnO_3$ as the major phase. Therefore, it is believed that the catalyst may be characterized as an amorphous/crystalline mixture where the only significant crystalline phase is $BaSnO3$ and the amorphous phase is a $YBaO_x$ oxide which homogeneously coats or forms a solid solution with the $BaSnO_3$. The composition of $BaSnO_3$ and $YBaO_x$ phases forms a uniquely uniform material.

Less severe conditions also caused the catalyst to become more homogeneous in composition yet still retain its selectivity to $C_2+$ hydrocarbons. For example, at 97% oxygen conversion, 800° C., 5:1 $CH_4/O_2$ feed at 20,000 cc/gm-hr space velocity (SV) and 4 hours reaction time, a large fraction of the areas had a composition near $Y_1Ba_2Sn_3O_y$. A majority of areas followed the tie line from $BaSnO_3$ to $Y_2O_3$, indicating varying amounts of $Y_2O_3$ are in solid solution or coating the $BaSnO_3$.

Elemental x-ray mapping of the used catalyst also confirmed the compositional homogeneity of the catalyst.

High resolution TEM showed lattice fringes on the $Y_1Ba_2Sn_3O_y$ catalyst which had been used at full oxygen conversion. At magnifications greater than 1,000,000X, fringe spacings of 5.5 Å, 7Å and 12.2 Å were observed. These are larger than pure $BaSnO_3$ at 4.117 Å and $Y_2Sn_2O_7$ at 10.4 Å. The expanded lattice seen in the TEM suggest some small particles which have incorporated other materials into the lattice such as yttria, i.e.,° solid solutions. $BaCO_3$ has cell dimensions of a=5.134 Å, b=8.9 Å and c=6.43 Å, some of which are similar to those observed by TEM.

All used catalysts show an increase in the homogeneity of composition, suggesting a unique mixture of crystalline and amorphous phase.

Example 15

X-Ray Diffraction Analysis

A sample of $Y_1Ba_2Sn_3O_y$ catalyst was calcined to 800° C. for 5 hours in air which resulted in a complex mixture of barium carbonate ($BaCO_3$), tin oxide ($SnO_2$) and minor poorly crystalline phases of barium stannate ($BaSnO_3$) and yttrium tin pyrochlore ($Y_2Sn_2O_7$) As shown in Example 17, below, Sn119 NMR chemical shifts suggested that neither the $Y_2Sn_2O_7$ nor the $BaSnO_3$ were solid solutions. Further calcination to 1100° C. increased the crystallinity and concentration of $BaSnO_3$ yet changed the catalysts selectivity to more combustion products. A significant decrease in $BaCO_3$ was also observed at this temperature. Further calcination to 1400° C. caused the disappearance of $BaCO_3$ and the major phases are now $BaSnO_3$ and a $Ba(Y)SnO_3$ solid solution which has an expanded cell of 4.1354 Å. Pure $Y_2Sn_2O_7$ was also present. The material stayed with this composition until the calcining temperature was close to 1700° C. at which the sample melted and reacted with the alumina crucible. $SnO_2$ observed in fresh catalysts had a preferred orientation such that the 101 and 202 XRD diffraction intensities were much greater than the intensities published in the powder diffraction files. Bulk $SnO_2$ prepared by calcination of the Sn(II) acetate starting materials also has the preferred orientation shown by the 101 and 202 reflection intensity enhancement. This feature is common to the oxidative coupling catalysts but is also found in $SnO_2$, a combustion catalyst prepared from tin acetate.

Depending on the reaction conditions, the used catalysts had significantly higher crystallinity and were more pure in $BaSnO_3$ than the fresh catalysts. The catalyst was in effect being crystallized to $BaSnO_3$ by being used for methane oxidative coupling. The higher the oxygen conversion, the larger the effect on the catalyst. For that matter, catalysts that had been heated too hot or run under reducing conditions (100% oxygen conversion) were some of the most crystalline with the major phase being pure $BaSnO_3$ along with minor phases of $Y_2Sn_2O_7$ solid solution, $SnO_2$, and another poorly crystalline $BaSnO_3$ solid solution phase. Barium carbonate, which was a major phase in the fresh catalyst had decomposed to form $BaSnO_3$ in the catalyst used at full oxygen conversion. $BaCO_3$ only exists in traces in the used catalyst. The amount of carbonate in the used catalysts depends on the severity of operation. The solid solution of $Y_2Sn_2O_7$ had an expanded cubic cell constant of 10.430(4) Å compared to the known value of 10.373 Å. The minor phase of $BaSnO_3$ solid solution had a cubic cell constant of 4.1209 Å compared to the known cell constant of 4.1163 Å. Expansion of the unit cell in both the $Y_2Sn_2O_7$ and $BaSnO_3$ is caused by yttria substituting for the smaller tin ion in the structure, thus creating a solid solution with yttria.

Example 16

XPS/Auger Analysis

Both fresh and used $Y_1Ba_2Sn_3O_y$ catalysts (fresh and used Compositions A of Example 1) were analyzed by Auger spectroscopy which uncovered an unusual phenomena with the fresh catalyst's Sn MNN Auger transition. Typical Sn MNN transitions observed with SnO (FIG. 10), $SnO_2$ (FIG. 11), $BaSnO_3$ (FIG. 12), and $Y_2Sn_2O_7$ (FIG. 13) shows both a $M_4N_{4,5}N_{4,5}$ and a $M_5N_{4,5}N_{4,5}$ transition; whereas, in the fresh $Y_1Ba_2Sn_3O_7$ catalyst (Composition A of Example 1) (FIGS. 1 and 3), the $M_4N_{4,5}N_{4,5}$ is rapidly quenched, i.e., it is not readily observed. $SnO_2$, prepared from the acetate, which has the unusually intense 101 and 202 XRD diffractions, has both the $M_4N_{4,5}N_{4,5}$ and $M_5N_{4,5}N_{4,5}$ transitions as does bulk $SnO_2$. Thus, the comparative absence of the $M_4N_{4,5}N_{4,5}$ peak in the $YBa_2SnO_4O_y$ composition of th does not appear to be due to the preferred orientation of the $SnO_2$ particles.

With respect to the XPS results, the binding energy shifts for fresh catalyst were consistent with the XRD results that showed the presence of $Y_2O_3$ and $SnO_2$. The optimized preparation using tin acetate had large amounts of $BaCO_3$ on the surface, whereas a preparation involving physically mixed pure oxides had Sn metal and a barium oxide with low binding energy shift of 778.2 eV. Pure $BaCO_3$ and BaO have binding energies of 779.0 and 779.7 eV. Low binding energies are also observed in the new superconductive $Y_1Ba_2Cu_3O_y$ where the barium is a layered perovskite structure.

Relative surface compositions were determined and found to be dependent on catalyst preparation. The preferred method of synthesis using tin acetate had an apparent surface enrichment of barium in the form of both carbonate and oxide and a depletion of tin when calcined to 800° C. Depth profiling showed that the composition was homogeneous throughout the bulk which suggests that the tin is in small (<2000Å) crystallites which make it appear to be in lower concentration by XPS. Catalyst prepared by physically mixing $Y_2O_3$, BaO and SnO and calcining to 800° C. had a surface enrichment of yttria and a depletion of barium and tin. Both catalysts had similar performance for methane oxidative coupling. The used catalyst prepared from tin acetate still had barium enrichment if reaction conditions were maintained below 100% oxygen conversion. A used catalyst that had been exposed to extreme reaction conditions such as 875° C. had yttria enrichment.

Figure 8:
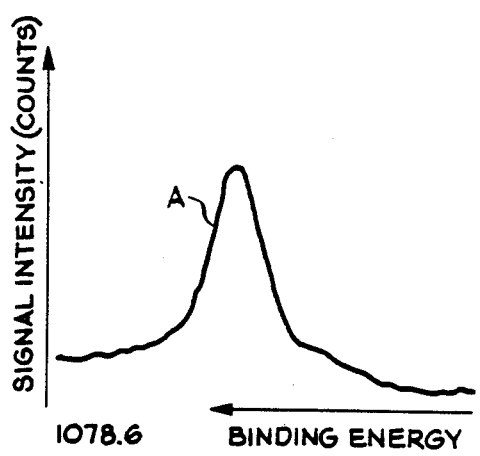
FIG. 8 is the Auger spectrum of fresh $Y_1Ba_2Sn_3O_y$ catalyst.
Figure 9:
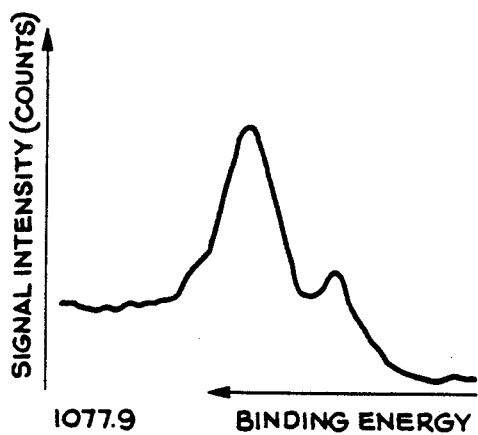
FIG. 9 is the Auger spectrum of used, overreduced $Y_1Ba_2Sn_3O_y$ catalyst.

The Auger line shapes of fresh and overreduced catalyst are best shown in FIG. 8 (same as shown in FIGS. 1 and 3 for Composition A of Example 1 but now shown without other spectra) and FIG. 9 respectively. As shown, the used catalyst (see FIG. 9) contains a 430.5 eV ±1 eV peak ("second peak") of sufficient size relative to the 424.5 eV ±1 eV peak ("first peak") that the ratio of the first peak to the second peak is not at least 10 to 1. In fact, for the Auger spectrum shown in FIG. 9, the ratio of these peak areas is more in the range of 8 to 1.

Example 17

Sn119 Solid State NMR

NMR analysis of fresh $Y_1Ba_2Sn_3O_y$ catalyst showed, that at the sensitivity of NMR, only known tin compounds were in the fresh catalyst. When calcined to 920° C., $SnO_2$ and a fairly broad peak for $BaSnO_3$ were observed. In a good, non-over-reduced catalyst, the Sn119 NMR is only slightly different from the fresh catalyst. A small increase in the $BaSnO_3$ peak was observed in the used catalyst. An 1100° C. calcination sharpened the $BaSnO_3$ peak, indicating better crystallinity, and a $Y_2Sn_2O_7$ pyrochlore was the only other species present. Integrated areas under these peaks corresponded well with XRD results in estimating compositions.

Example 18

Thermal Gravimetric Analysis

The fresh $Y_1Ba_2Sn_3O_y$ catalyst of Example 1 (Composition A) was calcined to about 800°-1000° C. in air. The material showed a gradual weight loss of about one (1) weight percent when heated to 800°-900° C. Such a small weight loss is attributed to the catalyst desorbing moisture or other volatile compounds adsorbed from the atmosphere and possible evolution of $CO_2$ from $BaCO_3$ decomposition at about 800° C. Cooling back to room temperature in dry air did not cause the catalyst to regain any of its lost weight.

Example 19

The catalyst of Example 1 (Composition A) was tested at 750° C. in a recycle reactor wherein the gases were well backmixed to illustrate the effect of complete oxygen conversion on selectivity to $C_2+$ hydrocarbons. The feed was 10:1 $CH_4/O_2+56\%$ nitrogen and the pressure was held at 3 psig. Two experiments were conducted so as to obtain a wide variation in contact time (grams of catalyst/sec/cc gas at STP): one with 0.5 gram catalyst and the other with 0.05 gram catalyst. Each run was made in the order of lowest to highest contact time. Selectivity to $C_2+$ hydrocarbons remains relatively constant until reaching a contact time of about 0.5 seconds; thereafter, $C_2+$ selectivity decreases as contact time increases. Upon reaching the longest contact time of 6, the initial contact time of 0.3 was repeated for the run with 0.5 gram catalyst. The $C_2+$ selectivity returned to 45% which is 10% below the original value of 55%, implying catalyst deactivation. Part of the fall off in $C_2+$ selectivity at contact times about 0.5 is attributed to the intrinsic response of the catalyst at high oxygen conversion; however, part of the drop is an accumulative, nonreversible decline from catalyst aging caused by reduction and degradation at complete oxygen conversion.

Example 20

A carbonate free $Y_1Ba_2Sn_3$ oxide catalyst was prepared by grinding $Y(NO_3)_3 \cdot 6H_2O$ (2.30 g), $Ba(OH)_2 \cdot 8H_2O$ (3.79 g) and $Sn(OCOCH_3)_3$ (4.2 g) under air or nitrogen to form a soft paste. The paste was extruded and fired in air at 100° C., 200° C., 300° C., 400° C., 500° C., 600° C. and 700° C. for 15-30 minutes at each temperature, then heated at 800° C. for 5 hours under air flow. The catalyst was then calcined at 900° C. for 1 hours, the temperature was reduce to 800° C. and the catalyst was calcined at that temperature for 2 hours. X-ray diffraction of the fresh catalyst showed $BaSnO_3$ as major, $Y_2O_3$ and $BaCO_3$ (Witherite phase) as intermediate, and $SnO_2$ as a minor crystalline material.

Example 21

The catalyst of Example 20 was ground and sieved to pass through a 180 mesh sieve and be held on a 250 mesh sieve. 50 milligrams of the catalyst, diluted with about 500 mg of alpha alumina, was tested with a fresh feed blend of 30% $CH_4$, 6% $O_2$, 56% $N_2$ at 100 standard cc per minute rate at 800° C. Ultra high purity gases were used. In addition, 250 cc/minute of the product gas at room temperature was recycled to the front of the unit. Near complete oxygen conversion was obtained (97%) and 20% of the methane was converted. Carbon atom selectivities were 59% to hydrocarbons with 2 or more carbon atoms, 2% to carbon monoxide, and 39% to carbon dioxide.

It is to be understood that the discussion of theory, such as the discussion regarding quantum mechanics and the mechanics of Auger electron spectroscopy, for example, are included to assist in the understanding of the subject invention and are in no way limiting of the invention.

The foregoing detailed description is given for clearance of understanding only, and no unnecessary limitations are to be understood therefrom, as modifications within the scope of the invention will be obvious to those skilled in the art.

What is claimed is:

1. A composition comprising oxidized tin and having a tin Auger line transition wherein the ratio of the area of the $M_5N_{4,5}N_{4,5}$ transition peak at 424.5 eV±1 eV, having a 6 eV FWHM, to the area of $M_4N_{4,5}N_{4,5}$ transition peak at 430.5 eV±1 eV is at least 10 to 1.

2. The composition of claim 1 additionally comprising an oxidized Group IIIB metal selected from the group consisting of yttrium, lanthanum and scandium.

3. The composition of claim 1 additionally comprising an oxidized Group IIA metal selected from the group consisting of magnesium, calcium, strontium and barium.

4. The composition of claim 3 wherein said Group IIA metal is barium.

5. The composition of claim 4 represented by the formula $BaSnO_y$ wherein y represents the number of oxygen anions required to balance the combined charge of the cationic species Ba and Sn.

6. The composition of claim 3 additionally comprising an oxidized Group IIIB metal selected from the group consisting of yttrium, lanthanum and scandium wherein the tin, Group IIA metal and Group IIIB metal are present in an approximate atomic ratio of 2-4 atoms of tin per 0.5-3 atoms of Group IIA metal per atom of Group IIIB metal.

7. The composition of claim 6 wherein said Group IIIB metal is yttrium and said Group IIA metal is barium.

8. The composition of claim 7 wherein yttrium, barium and tin are present in an atomic ratio of 1:2:3, respectively.

9. A composition comprising: (a) a Group IIA metal selected from the group consisting of magnesium, calcium, strontium and barium; (b) tin and (c) oxygen, having a tin Auger line transition wherein the ratio of the area of the $M_5N_{4,5}N_{4,5}$ transition peak at 424.5 eV ±1 eV, having a 6 eV FWHM, to the area of the $M_4N_{4,5}N_{4,5}$ transition peak at 430.5 eV±1 eV is at least 10 to 1.

10. The composition of claim 9 additionally comprising a Group IIIB metal selected from the group consisting of yttrium, lanthanum and scandium.

11. The composition of claim 10 wherein the Group IIIB metal, Group IIA metal and tin are present in the approximate atomic ratio of 1:0.5–3:2–4, respectively.

12. The composition of claim 11 wherein said Group IIA metal is barium.

13. The composition of claim 12 wherein the Group IIIB metal is yttrium, and wherein the yttrium, barium and tin are present in an approximate atomic ratio of about 1:2:3, respectively.

14. The composition of claim 9 prepared by a process comprising intimately mixing an oxygen-containing compound of said Group IIA metal with tin (II) acetate having a stoichiometric excess of acetic acid followed by calcining the mixture to a selected temperature.

15. The composition of claim 14 wherein said Group IIA metal is barium.

16. The composition of claim 14 additionally comprising a Group IIIB metal selected from the group consisting of yttrium, lanthanum and scandium wherein during said preparation process oxygen-containing compounds of each of said Group IIIB metal and Group IIA metal are intimately mixed with tin (II) acetate having a stoichiometric excess of acetic acid followed by calcining the mixture to a selected temperature.

17. The composition of claim 16 wherein said Group IIIB metal is yttrium and said Group IIA metal is barium.

18. An oxidative coupling catalyst composition useful in the conversion of a feedstock alkane containing from 1 to 4 carbon atoms to higher molecular weight hydrocarbon, said composition comprising: (a) an oxidized Group IIA metal selected from the group consisting of magnesium, calcium, strontium and barium; and (b) oxidized tin wherein the tin and Group IIA metal are present in an approximate atomic ratio of 2–4 atoms of tin per 0.5–3 atoms of Group IIA metal, said composition having a tin Auger line transition wherein the ratio of the area of the $M_5N_{4,5}N_{4,5}$ transition peak at 424.5 eV±1 eV, having a 6 eV FWHM, to the area of the $M_4N_{4,5}N_{4,5}$ transition peak at 430.5 eV±1 eV is at least 10 to 1.

19. The catalyst composition of claim 18 additionally comprising a Group IIIB metal selected from the group consisting of yttrium, lanthanum and scandium wherein the Group IIIB metal, Group IIA metal and tin are present in an atomic ratio of approximately 1:0.5–3:2–4, respectively.

20. The catalyst composition of claim 18 wherein said Group IIA metal is barium.

21. The catalyst composition of claim 20 wherein the Group IIIB metal is yttrium and wherein the yttrium, barium and tin are present in an approximate atomic ratio of about 1:2:3, respectively.

22. The catalyst composition of claim 18 prepared by a method comprising intimately mixing an oxygen-containing compound of said Group IIA metal with tin (II) acetate having a stoichiometric excess of acetic acid followed by calcining the mixture to a selected temperature.

23. The catalyst composition of claim 22 said Group IIA metal is barium.

24. The catalyst composition of claim 22 additionally comprising a Group IIIB metal selected from the group consisting of yttrium, lanthanum and scandium wherein during said preparation method oxygen-containing compounds of each of said Group IIIB metal and Group IIA metal are intimately mixed with tin (II) acetate having a stoichiometric excess of acetic acid followed by calcining the mixture to a selected temperature.

25. The catalyst composition of claim 24 wherein said Group IIIB metal comprises yttrium and said Group IIA metal comprises barium.

26. An oxidative coupling catalyst composition useful in the conversion of a feedstock alkane containing from 1 to 4 carbon atoms to a higher molecular weight hydrocarbon, said composition comprising: (a) oxidized yttrium; (b) oxidized barium; and (c) oxidized tin wherein the tin barium and yttrium are present in an approximate atomic ratio of 2–4 atoms of tin per 0.5–3 atoms of barium per atom of yttrium, said catalyst composition having a tin Auger line transition wherein the ratio of the area of the $M_5N_{4,5}N_{4,5}$ transition peak at 424.5 eV±1 eV, having a 6 eV FWHM, to the area of the $M_4N_{4,5}N_{4,5}$ transition peak at 430.5 eV±1 eV is at least 10 to 1.

27. The catalyst composition of claim 26 wherein the yttrium, barium and tin are present in an approximate atomic ratio of about 1:2:3, respectively.

28. The catalyst composition of claim 26 prepared by a method comprising intimately mixing yttrium carbonate and barium hydroxide with tin II acetate having a stoichiometric excess of acetic acid followed by calcining the mixture to a selected temperature.

* * * * *

UNITED STATES PATENT OFFICE
CERTIFICATE OF CORRECTION

Page 1 of 2

Patent No. 4,971,940                    Dated November 20, 1990

Inventor(s) Mark P. Kaminsky, Mark S. Kleefisch, Gerry W. Zajac

It is certified that error appears in the above-identified patent and that said Letters Patent is hereby corrected as shown below:

| Col. | Line | |
|---|---|---|
| 5 | 6 | "catalysts" should be --catalyst-- |
| 6 | 44 | "X1-4" should be --X1-X4-- |
| 6 | 50 | "$M_5N_{4,5}N4.5$" should be --$M_5N_{4,5}N_{4,5}$-- |
| 9 | 47 | "$YBa_2SN_3O_y$" should be --$YBa_2Sn_3O_y$-- |
| 10 | 13 | "ethyleleglycoxide" should be --ethyleneglycoxide-- |
| 13 | 16 | "875" should be --875°-- |
| 17 | 55 | "$YO_1.5$" should be --$YO_{1.5}$-- |
| 18 | 56 | "BaSnO3" should be --$BaSnO_3$-- |
| 18 | 65 | "20,000" should be --120,000-- |
| 19 | 14 | "i.e.,°" should be --i.e.,-- |
| 20 | 26 | "$YBa_2SnO_4O_y$" should be --$YBa_2Sn_3O_y$-- |
| 21 | 68 | "reduce" should be --reduced-- |

UNITED STATES PATENT OFFICE
CERTIFICATE OF CORRECTION

Patent No. 4,971,940   Dated November 20, 1990

Inventor(s) Mark P. Kaminsky, Mark S. Kleefisch, Gerry W. Zajac

It is certified that error appears in the above-identified patent and that said Letters Patent is hereby corrected as shown below:

Patent reads

| Col. | Line | | |
|---|---|---|---|
| 20 | 27 | "of th does" should be | --of the invention does-- |
| 1 | 24 | "gas, and mainly" should be | --gas, mainly-- |

Signed and Sealed this

Fourteenth Day of July, 1992

Attest:

DOUGLAS B. COMER

Attesting Officer   Acting Commissioner of Patents and Trademarks